(12) United States Patent
Bailey et al.

(10) Patent No.: US 6,790,664 B2
(45) Date of Patent: Sep. 14, 2004

(54) FLUOROMETRIC MONITORING AND CONTROL OF SOLUBLE HARDNESS OF WATER USED IN INDUSTRIAL WATER SYSTEMS

(75) Inventors: Bruce R. Bailey, Tuttle, OK (US); Xiaojun Dang, Naperville, IL (US); David A. Grattan, LaGrange, IL (US); Linda Link, Carol Stream, IL (US)

(73) Assignee: Nalco Company, Naperville, IL (US)

( * ) Notice: Subject to any disclaimer, the term of this patent is extended or adjusted under 35 U.S.C. 154(b) by 474 days.

(21) Appl. No.: 10/033,756

(22) Filed: Dec. 28, 2001

(65) Prior Publication Data

US 2003/0124730 A1 Jul. 3, 2003

(51) Int. Cl.⁷ .............................................. G01N 21/64
(52) U.S. Cl. ............................ 436/55; 436/172; 436/79
(58) Field of Search ........................... 436/55, 79, 172; 422/62, 82.07, 82.08

(56) References Cited

U.S. PATENT DOCUMENTS

| | | |
|---|---|---|
| 4,783,314 A | 11/1988 | Hoots et al. |
| 4,966,711 A | 10/1990 | Hoots et al. |
| 4,992,380 A | 2/1991 | Moriarty et al. |
| 5,006,311 A | 4/1991 | Hoots et al. |
| 5,043,406 A | 8/1991 | Fong |
| 5,171,450 A | 12/1992 | Hoots |
| 5,278,074 A | 1/1994 | Rao et al. |
| 5,378,784 A | 1/1995 | Fong et al. |
| 5,389,548 A | 2/1995 | Hoots et al. |
| 5,411,889 A | 5/1995 | Hoots et al. |
| 5,413,719 A | 5/1995 | Sivakumar et al. |
| 5,645,799 A | 7/1997 | Shah et al. |
| 5,658,798 A | 8/1997 | Bertin et al. |
| 5,702,684 A | 12/1997 | McCoy et al. |
| 5,714,387 A | 2/1998 | Fowee et al. |
| 5,736,405 A | 4/1998 | Alfano et al. |
| 5,919,707 A | 7/1999 | Banks et al. |
| 5,958,788 A | 9/1999 | Johnson et al. |
| 5,986,030 A | 11/1999 | Murray et al. |
| 6,599,748 B1 * | 7/2003 | Nakajima et al. .............. 436/39 |
| 2004/0098202 A1 * | 5/2004 | McNeil et al. ................. 702/12 |

FOREIGN PATENT DOCUMENTS

| | | | |
|---|---|---|---|
| DE | 2949254 A1 | * | 6/1981 |
| WO | WO 02/084278 A1 | * | 10/2002 |
| WO | WO 03/058218 A1 | * | 7/2003 |

OTHER PUBLICATIONS

Zhang, Ji et al, "Colorimetric method and instrument for rapidly measuring hardness of boiler water" Chemical Abstracts, vol. 123, Abstract No. 92743 (1995).*

Venkataraman, K. et al, "Indicators for estimation of hardness in brine used in membrane–type chlor–alkali cells" Chemical Abstracts, vol. 112, Abstract No. 68787 (1990).*

Amelin, V.G., "Test method for the determinationof overall quality characteristics of water using indicator papers" Chemical Abstracts, vol. 132, Abstract No. 352369 (2000).*

Imato, T. et al, "Flow injection determination of total water hardness in seawater by using metal–ligand buffer and color–indicator" Chemical Abstracts, vol. 120, Abstract No. 172935 (1994).*

* cited by examiner

Primary Examiner—Jeffrey R. Snay
(74) Attorney, Agent, or Firm—Margaret M. Brumm; Thomas M. Breininger

(57) ABSTRACT

A method of monitoring and controlling hardness in an industrial water system is described and claimed. The method requires the use of a Compound that develops a separate detectable fluorescent signal in the presence of soluble hardness. A fluorometer is used to detect this separate detectable fluorescent signal of the Compound. The separate detectable fluorescent signal is used to ascertain the amount of soluble hardness present in the industrial water system.

28 Claims, No Drawings

FLUOROMETRIC MONITORING AND CONTROL OF SOLUBLE HARDNESS OF WATER USED IN INDUSTRIAL WATER SYSTEMS

FIELD OF INVENTION

This invention is in the field of industrial water systems. Specifically, this invention is in the field of monitoring and controlling soluble hardness in water in industrial water systems.

BACKGROUND OF THE INVENTION

Hardness in industrial waters is a term that refers to the amount of calcium and magnesium cations present in said waters and is usually expressed as ppm $CaCO_3$ equivalents. "Soluble hardness" refers to soluble $Ca^{+2}$ and $Mg^{+2}$ cations present in water. "Particulate hardness" or "colloidal hardness" refers to hardness that is insoluble (or "non-soluble"). Insoluble hardness water with acid and heat. Soluble hardness concentrations in the water of most industrial water systems can range from less than about 1 ppm to about several thousand ppm.

The process by which soluble species precipitate from the water in a boiler onto a surface is usually referred to as "scaling". The previously soluble salts then precipitate or form "scale" itself on the interior surfaces of the boiler. The presence of soluble hardness in the water of a boiler can lead to unwanted scaling resulting in the formation of scale on the interior surfaces of the boiler.

The process by which insoluble species suspended in water are 'left behind' and adhere to surfaces is usually referred to as "deposition" and the insoluble species that adhere to surfaces is typically referred to as a "deposit". In a boiler, this is of most concern at the areas where a wet/dry interface is present. This wet/dry interface is where the steam bubble is initiated, grows, and then detaches from the surface. Insoluble matter can collect and adhere at the interface of the bubble to the surface as it grows. With detachment of the steam bubble, the insoluble matter may adhere to the surface forming a deposit. These deposits are unwanted as their presence disrupts the heat transfer from the surface to the water.

The presence of soluble hardness in industrial waters typically leads to precipitation of those cations as scale on heat transfer surfaces of industrial process equipment. The presence of scale is detrimental to many individual units of industrial process equipment as well as to the industrial water system itself. Systems affected negatively by scale deposits include boilers, multi-stage evaporators, cooling water heat exchangers, cooling towers, hot water heaters, continuous casters, heat recovery steam generators, pipe surfaces and any other heat transfer surfaces of equipment present in industrial water systems.

Scale deposits are undesirable because deposited scale can cause impedance of flow, loss of cooling and reduced heat transfer capability, and "under deposit" corrosion problems. Under deposit corrosion problems are caused when chemical species which lead to corrosion (such as hydroxyl ions) concentrate to a point significantly higher than that found in the boiler bulk water. These high concentrations are more corrosive and can lead to tube failure.

Scale deposits are also undesirable because they can provide an environment that allows microbiological attachment and growth leading to microbiological induced corrosion problems. These undesirable situations can ultimately result in equipment failure such as boiler tube ruptures and heat exchanger failures, and unscheduled outages where it is not possible to operate the equipment. All of these undesirable situations can lead to a loss of capital equipment with resultant loss of production time and money.

It is common to monitor the soluble hardness in the water of an industrial water system and to treat industrial water systems such that soluble hardness does not scale and insoluble hardness does not deposit. The treatment products used to treat water are many and varied. "Scale inhibitors" are typically defined as chemical treatments that are added to water which reduce or eliminate the scaling process. "Dispersants" are typically defined as chemical treatments that are added to water to reduce or eliminate the accumulation of insoluble species as deposits on surfaces. When the insoluble matter is dispersed, it typically is not able to deposit. If the insoluble matter remains dispersed then it can be "carried away" in the natural flow patterns of the industrial water system.

Treatment products for industrial waters to remove, inhibit or control the detrimental effects of scale and deposits caused by the presence of soluble and insoluble hardness present in said waters are well known. Chemical treatment methods useful to treat water for undesirable hardness, based on soluble hardness, include such methods as coagulation, flocculation, precipitation, chelation, sequestration, complexation, dispersion and crystal modification. Treatment products include any anionic polymer that can effectively complex with magnesium; these anionic polymers include polyacrylates, polymethacrylates, and acrylate styrene sulfonate copolymers; chelants such as ethylenediaminetetraacetic acid, nitrilotriacetic acid, 1-hydroxyethylidene-1,1-diphosphonic acid, hexamethylenediaminetetra methylene phosphonic acid; phosphates such as hexametaphosphate, tripolyphosphate and ortho phosphate; polyphosphonates, natural and synthetic cationic polymers such as lignins, lignosulfonates, tannins, poly peptides, polyamines, quaternary amines, celluloses, starches, polymaleic anhydrides, polyvinyl sulfonates, inorganic phosphates, organic phosphates, inorganic carbonates, organic carbonates, various surfactants and known salts thereof.

There are industry standards for hardness in the water of industrial water systems. The American Society of Mechanical Engineers (ASME) has published a consensus on operating practices for the control of boiler feedwater and boiler water chemistry in modem industrial boilers. The ASME along with other organizations such as the Electric Power Research Institute ("EPRI"), British Boiler Manufacturers, Japanese Boiler Manufactures, German (VGB) boiler feedwater and boiler water guidelines for boiler systems, specify the acceptable maximum amount of hardness in feedwater to minimize the potential for hardness scale deposit problems that can lead to boiler failures.

The amount of soluble hardness present in industrial waters can change rapidly. If this change in soluble hardness goes unnoticed and the amount of treatment product for soluble hardness is unchanged in the water, the change in soluble hardness will result in under dosing or overdosing of the treatment products that are used to control, inhibit or eliminate the detrimental scaling of soluble hardness and depositing of insoluble hardness.

There are a number of known methods to measure and monitor soluble hardness in industrial waters. Some of these known methods include using sophisticated, time-consuming and expensive instrumentation such as Atomic Absorption Spectrophotometers and Inductively Coupled Argon Plasma Emission Spectrophotometers. Colorimetric methods include visual as well as instrumentation methods. Colorimetric methods that do not require expensive instrumentation include titration techniques that use indicator dyes sensitive to hardness which change color to the naked eye in the presence (or with some dyes, in the absence) of hardness. The known methods are subject to interferences, are known to be time consuming and the visual colorimetric methods can be very subjective based on subtle-to-the-eye distinctions in color changes.

It would be desirable to have a relatively inexpensive, reliable, non-colorimetric method for determining the level of soluble hardness in the water of an industrial water system.

SUMMARY OF THE INVENTION

The first aspect of the instant claimed invention is a method of determining the amount of soluble hardness in the water of an industrial water system comprising the steps of:

1) providing an industrial water system;
2) providing a Compound, wherein said Compound is selected from the group of chemicals that develop a separate detectable fluorescent signal in the presence of soluble hardness;
3) extracting a sample of water from the industrial water system and determining whether the sample of water is at or below the maximum temperature of operability of said Compound, and if the sample of water is above the maximum temperature of operability of said Compound, then cooling said sample of water until the temperature of the sample of water is at or below the maximum temperature of operability of said Compound;
4) measuring the pH of the sample of water and determining whether the pH is between about 7.5 and about 13.5 and if the pH is not between about 7.5 and about 13.5, adjusting the pH of the sample of water such that the pH is between about 7.5 and about 13.5;
5) adding to said sample of water from about 1 ppb to about 3,000 ppm of said Compound;
6) providing a fluorometer;
7) using said fluorometer to measure the separate detectable fluorescent signal of said Compound in said sample of water; and
8) using said separate detectable fluorescent signal to determine the amount of soluble hardness in said sample of water.

The second aspect of the instant claimed invention is a method of determining the amount of soluble hardness in the water of an industrial water system comprising the steps of:

1) providing an industrial water system wherein the pH of the water in said industrial water system is between about 7.5 and about 13.5;
2) providing a Compound, wherein said Compound is selected from the group of chemicals that develops a separate detectable fluorescent signal in the presence of soluble hardness;
3) adding to the water of the industrial water system from about 1 ppb to about 3,000 ppm of said Compound, wherein said Compound is added to the water of the industrial water system at a point where the water is at or below the maximum temperature of operability of said Compound;

4) providing a fluorometer;
5) using said fluorometer to measure the separate detectable fluorescent signal of said Compound in said water of said industrial water system; and
6) using said separate detectable fluorescent signal to determine the amount of soluble hardness in said water of said industrial water system.

The third aspect of the instant claimed invention is a method of determining whether the appropriate level of treatment product has been added to the water of an industrial water system comprising the steps of:

1) providing a treatment product, wherein said treatment product comprises scale inhibitor or dispersant or both, and an inert tracer in known proportions;
2) providing an industrial water system;
3) adding said treatment product to the water of said industrial water system;
4) providing a Compound, wherein said Compound is selected from the group of chemicals that develop a separate detectable fluorescent signal in the presence of soluble hardness;
5) extracting a sample of water from the industrial water system and determining whether the sample of water is at or below the maximum temperature of operability of said Compound, and if the sample of water is above the maximum temperature of operability of said Compound, then cooling said sample of water until the temperature of the sample of water is at or below the maximum temperature of operability of said Compound; wherein said sample of water is extracted from the industrial water system at a point where the water in the industrial water system has not had a treatment product added;
6) measuring the pH of the sample of water and determining whether the pH is between about 7.5 and about 13.5 and if the pH is not between about 7.5 and about 13.5, adjusting the pH of the sample of water such that the pH is between about 7.5 and about 13.5;
7) adding to said sample of water from about 1 ppb to about 3,000 ppm of said Compound;
8) providing at least one fluorometer;
9) using said fluorometer to measure the separate detectable fluorescent signal of said Compound in said sample of water;
10) using said separate detectable fluorescent signal to determine the amount of soluble hardness in said sample of water; and
11) increasing the feed rate of treatment product if step 10) shows there is an unacceptable level of soluble hardness present in the water and decreasing or maintaining the feed rate of treatment product if step 10) shows that an unacceptable level of soluble hardness is not present in the sample of water; wherein the amount of treatment product being fed into the water is verified by
  a) measuring the fluorescent signal of the inert tracer in said treatment product to determine how much inert tracer is present in the water; and
  b) using the amount of inert tracer present to determine the amount of treatment product that is being fed into the water.

The fourth aspect of the instant claimed invention is a method of determining whether the appropriate level of treatment product has been added to the water of an industrial water system comprising the steps of:

1) providing a treatment product, wherein said treatment product comprises scale inhibitor or dispersant or both, and an inert tracer in known proportions;
2) providing an industrial water system wherein the pH of the water in said industrial water system is between about 7.5 and about 13.5;
3) adding said treatment product to the water of said industrial water system;
4) providing a Compound, wherein said Compound is selected from the group of chemicals that develops a separate detectable fluorescent signal in the presence of soluble hardness;
5) adding to the water of the industrial water system from about 1 ppb to about 3,000 ppm of said Compound, wherein said Compound is added to the water of the industrial water system at a point where the water is at or below the maximum temperature of operability of said Compound;
6) providing at least one fluorometer;
7) using said fluorometer to measure the separate detectable fluorescent signal of said Compound in said water of said industrial water system; wherein the measurement takes place at a point where the water in the industrial water system has not had a treatment product added;
8) using said separate detectable fluorescent signal of said Compound to determine the amount of soluble hardness in said water, increasing the feedrate of treatment product if step 7) shows there is an unacceptable level of soluble hardness present in the water and decreasing or maintaining the feed rate of treatment product if step 7) shows that an unacceptable level of soluble hardness is not present in the water; wherein the amount of treatment product being fed into the water is verified by:
   a) measuring the fluorescent signal of the inert tracer in said treatment product to determine how much inert tracer is present in the water; and
   b) using the amount of inert tracer present to determine the amount of treatment product that is present in the water.

The fifth aspect of the instant claimed invention is a method of determining whether the appropriate level of Selected Treatment Product has been added to the water of an industrial water system comprising the steps of:
1) providing a Selected Treatment Product, wherein said Selected Treatment Product comprises a Selected Scale Inhibitor or Selected Dispersant or both, and an inert tracer in known proportions;
2) providing an industrial water system;
3) adding said Selected Treatment Product to the water of said industrial water system;
4) providing a Compound, wherein said Compound is selected from the group of chemicals that develop a separate detectable fluorescent signal in the presence of soluble hardness;
5) extracting a sample of water from the industrial water system and determining whether the sample of water is at or below the maximum temperature of operability of said Compound, and if the sample of water is above the maximum temperature of operability of said Compound, then cooling said sample of water until the temperature of the sample of water is at or below the maximum temperature of operability of said Compound;
6) measuring the pH of the sample of water and determining whether the pH is between about 7.5 and about 13.5 and if the pH is not between about 7.5 and about 13.5, adjusting the pH of the sample of water such that the pH is between about 7.5 and about 13.5;
7) adding to said sample of water from about 1 ppb to about 3,000 ppm of said Compound;
8) providing at least one fluorometer;
9) using said fluorometer to measure the separate detectable fluorescent signal of said Compound in said sample of water;
10) using said separate detectable fluorescent signal to determine the amount of soluble hardness in said sample of water; and
11) increasing the feed rate of Selected Treatment Product if step 10) shows there is an unacceptable level of soluble hardness present in the water and decreasing or maintaining the feed rate of Selected Treatment Product if step 10) shows that an unacceptable level of soluble hardness is not present in the sample of water; wherein the amount of Selected Treatment Product being fed into the water is verified by
   a) measuring the fluorescent signal of the inert tracer in said Selected Treatment Product to determine how much inert tracer is present in the water; and
   b) using the amount of inert tracer present to determine the amount of Selected Treatment Product that is being fed into the water.

The sixth aspect of the instant claimed invention is a method of determining whether the appropriate level of Selected Treatment Product has been added to the water of an industrial water system comprising the steps of:
1) providing a Selected Treatment Product, wherein said Selected Treatment Product comprises Selected Scale Inhibitor or Selected Dispersant or both, and an inert tracer in known proportions;
2) providing an industrial water system wherein the pH of the water in said industrial water system is between about 7.5 and about 13.5;
3) adding said Selected Treatment Product to the water of said industrial water system;
4) providing a Compound, wherein said Compound is selected from the group of chemicals that develops a separate detectable fluorescent signal in the presence of soluble hardness;
5) adding to the water of the industrial water system from about 1 ppb to about 3,000 ppm of said Compound; wherein said Compound is added to the water of the industrial water system at a point where the water is at or below the maximum temperature of operability of said Compound;
6) providing at least one fluorometer;
7) using said fluorometer to measure the separate detectable fluorescent signal of said Compound in said water of said industrial water system;
8) using said separate detectable fluorescent signal of said Compound to determine the amount of soluble hardness in said water, increasing the feed rate of Selected Treatment Product if step 7) shows there is an unacceptable level of soluble hardness present in the water and decreasing or maintaining the feed rate of Selected Treatment Product if step 7) shows that an unacceptable level of soluble hardness is not present in the water; wherein the amount of Selected Treatment Product being fed into the water is verified by:

a) measuring the fluorescent signal of the inert tracer in said Selected Treatment Product to determine how much inert tracer is present in the water; and b) using the amount of inert tracer present to determine the amount of Selected Treatment Product that is present in the water.

DETAILED DESCRIPTION OF THE INVENTION

Throughout this patent application the following terms have the indicated definitions:

"aka" means "also known as".

ALDRICH refers to Aldrich, P.O. Box 355, Milwaukee, Wis. 53201 USA., telephone number (800) 558-9160.

CAS Registry No. refers to the Chemical Abstracts Service Registry No. for a Compound.

"soluble hardness" refers to soluble $Ca^{+2}$ and $Mg^{+2}$ cations present in said waters.

"particulate hardness" or "colloidal hardness" refers to hardness that is not soluble or is "insoluble". Insoluble hardness is not capable of interacting with a Compound that develops a separate detectable fluorescent signal in the presence of soluble hardness. Non-soluble hardness can be converted to soluble hardness by treating the water with acid and heat.

Nalco refers to ONDEO Nalco Company, ONDEO Nalco Center, 1601 W. Diehl Road, Naperville Ill. 60563, telephone number (630) 305-1000.

"nm" refers to nanometers.

"ppb" refers to parts per billion.

"ppm" refers to parts per million.

The first aspect of the instant claimed invention is a method of determining the amount of soluble hardness in the water of an industrial water system comprising the steps of:

1) providing an industrial water system;
2) providing a Compound, wherein said Compound is selected from the group of chemicals that develop a separate detectable fluorescent signal in the presence of soluble hardness;
3) extracting a sample of water from the industrial water system and determining whether the sample of water is at or below the maximum temperature of operability of said Compound, and if the sample of water is above the maximum temperature of operability of said Compound, then cooling said sample of water until the temperature of the sample of water is at or below the maximum temperature of operability of said Compound;
4) measuring the pH of the sample of water and determining whether the pH is between about 7.5 and about 13.5 and if the pH is not between about 7.5 and about 13.5, adjusting the pH of the sample of water such that the pH is between about 7.5 and about 13.5;
5) adding to said sample of water from about 1 ppb to about 3,000 ppm of said Compound;
6) providing a fluorometer;
7) using said fluorometer to measure the separate detectable fluorescent signal of said Compound in said sample of water;
8) using said separate detectable fluorescent signal to determine the amount of soluble hardness in said sample of water.

The method of the instant claimed invention is useful to determine soluble hardness in the water of an industrial water system. Suitable industrial water systems include cooling tower water systems (including open recirculating, closed and once-through cooling tower water systems); petroleum wells, downhole formations, geothermal wells and other oil field applications; boilers and boiler water systems; mineral process waters including mineral washing, flotation and benefaction; paper mill digesters, washers, bleach plants and white water systems; black liquor evaporators in the pulp industry; gas scrubbers and air washers; continuous casting processes in the metallurgical industry; air conditioning and refrigeration systems; industrial and petroleum process water; indirect contact cooling and heating water, such as pasteurization water; water reclamation and purification systems; membrane filtration water systems; food processing streams including meat, vegetable, sugar beets, sugar cane, grain, poultry, fruit and soybean; and waste treatment systems as well as in clarifiers, liquid-solid applications, municipal sewage treatment and industrial or municipal water systems. Preferred industrial water systems include cooling towers and boilers.

Compounds that develop a separate detectable fluorescent signal in the presence of soluble hardness are selected from the group consisting of Compounds comprising an azo group (—N═N—)and at least two aromatic rings, wherein the aromatic rings may have substituents that are positioned ortho to the azo group and wherein the substituents are selected such that they are capable of forming a cyclic complex upon reaction of the Compound with soluble hardness. It is acknowledged by Applicants that any Compound suitable for use in the methods of the instant claimed invention probably would have its own detectable fluorescent signal. It is believed, without intending to be bound thereby, that the Compound interacts with the soluble hardness in such a way that a new moiety is formed and it is this new moiety that has the separate detectable fluorescent signal. The phrase "separate" is used to make sure that it is understood that this invention is not concerned with the fluorescent signal of the Compound itself, but only with the separate detectable fluorescent signal that indicates the presence of soluble hardness.

Within this group of Compounds, preferred Compounds are selected from the group
consisting of the following acids and all of their known salts.

Benzenesulfonic acid, 4-hydroxy-3-{(2-hydroxy-1-naphthalenyl)azo}-,

1-Naphthalenesulfonic acid, 3-hydroxy-4-{(2-hydroxy-5-methylphenyl)azo}-,

1-Naphthalenesulfonic acid, 3-hydroxy-4-{(1-hydroxy-2-naphthalenyl)azo}-, and 2,7-Naphthalenedisulfonic acid, 3-{(5-chloro-2-hydroxyphenyl)azo}-4,5-dihydroxy-.

The most preferred Compounds are

Benzenesulfonic acid, 4-hydroxy-3-{(2-hydroxy-1-naphthalenyl)azo}-, monosodium salt aka Acid Alizarin Violet N, CAS Registry No. 2092-55-9;

1-Naphthalenesulfonic acid, 3-hydroxy-4-{(2-hydroxy-5-methylphenyl)azo}-, aka

Calmagite, CAS Registry No. 3147-14-6;

1-Naphthalenesulfonic acid, 3-hydroxy-4-{(1-hydroxy-2-naphthalenyl)azo}-, monosodium salt, aka Eriochrome® Blue Black B, CAS Registry No. 3564-14-5; and 2,7-Naphthalenedisulfonic acid, 3-{(5-chloro-2-hydroxyphenyl)azo}-4,5-dihydroxy-, disodium salt, aka Plasmocorinth B, CAS Registry No. 1058-92-0.

As mentioned previously these Compounds have an existing fluorescent signal in water. The excitation (hereinafter "EX") and emission (hereinafter "EM") wavelengths for each of the four preferred Compounds are as follows.

| Compound | Wavelengths |
|---|---|
| Acid Alizarin Violet N | 300 nm EX, 410 nm EM |
|  | 240 nm EX, 410 nm EM |
| Calmagite | 355 nm EX, 420 nm EM |
|  | 290 nm EX, 420 nm EM |
|  | 245 nm EX, 420 nm EM |
| Eriochrome ® Blue Black B | 355 nm EX, 420 nm EM |
|  | 290 nm EX, 420 nm EM |
|  | 245 nm EX, 420 nm EM |
| Plasmocorinth B | 225 nm EX, 335 nm EM |
|  | 285 nm EX, 335 nm EM |

The reason these four Compounds are preferred is that in addition to their known fluorescent signals, all four of these Compounds develop a separate detectable fluorescent signal in the presence of hardness attributed to magnesium. (Only Plasmocorinth B has distinct features that make it possible, using fluorescence and absorbance analytical techniques to quantify and differentiate between calcium and magnesium.) It is the development of this separate detectable fluorescent signal in the presence of hardness that make it possible to use these Compounds in all aspects of the instant claimed invention.

In order to facilitate the reaction of the Compound with the soluble hardness in the water, it is necessary for the pH in the water to be between about 7.5 and about 13.5, more preferably the pH of water should be between about 8.5 and about 13, and most preferably the pH of water should be between about 9.5 and 12.5. If the pH of the water is already between these two levels, then nothing further need be done. If the pH of the water is not already between these two levels, then the pH must be adjusted, using typical pH adjusting reagents, such as acids and bases, such that the pH is between these two levels.

Alternatively, it is possible to formulate the Compound with a buffer such that the pH of the water itself need not be adjusted as the buffer ensures the pH is between about 7.5 and 13.5. Buffers suitable for this purpose are known to people of ordinary skill in the art of buffers.

The maximum temperature of operability for each Compound capable of being used in the methods of the instant claimed invention can be determined by putting the Compound into water with a known amount of soluble hardness and raising the temperature of the water, while measuring the separate detectable fluorescent signal of the moiety. The four preferred Compounds have been tested in this way using a TRASAR®350 fluorometer, available from Nalco.

The four preferred Compounds, Acid Alizarin Violet N, Calmagite, Eriochrome® Blue Black B and Plasmocorinth B, were found to be stable for a duration of at least about 5 minutes from above the freezing point of the water they are tested in to about 176.7° C. (equivalent to 350° F.). Therefore, the maximum temperature of operability for these four Compounds is at least about 176.7° C.

It is also true that the time needed for detecting a fluorescent signal is very short, usually less than about 30 seconds, therefore it is possible that these Compounds may actually function adequately at temperatures above 176.7° C. for a time period long enough to detect and measure the separate detectable fluorescent signal of the Compound. Before using any of these Compounds, or any other suitable Compounds in an operating industrial water system it is recommended that laboratory testing be conducted using the process water, where the test is conducted with the process water being kept at the operating temperature of the water in the industrial water process.

It is preferred that fluorometric measurements be done as close as possible to room temperature of about 25° C. If it is not possible to make the fluorometric measurement at room temperature then people of ordinary skill in the art of fluorometry know how to perform the necessary "temperature correction for a fluorometer" required in order to report an accurate fluorescent signal.

The Compounds only develop a separate detectable fluorescent signal upon contact with soluble hardness when the water is at temperatures at or below the maximum temperature for operability of each Compound. Therefore, either a part of the industrial water system where the water is at or below the operability temperature must be chosen for the point of addition of the Compound to the water of the industrial water system, as described in the second and fourth and sixth aspects of the instant claimed invention, or a sample of water is extracted from the industrial water system and its temperature determined and, if necessary, adjusted to be at or below the operability temperature of the Compound, as described in the first, third and fifth aspects of the instant claimed invention.

The preferred amount of Compound added to the water of said industrial water system is from about 1 ppb to about 3,000 ppm. The more preferred amount of Compound is from about 50 ppb to about 100 ppm. The most preferred amount of Compound is from about 100 ppb to about 10 ppm.

The method of addition of the Compound to the water of the industrial water system depends upon what industrial water system is being treated and the Compound selected. In determining what point to add the Compound to the water of the industrial water system, it is necessary to understand what the temperature is at various locations in the industrial water system. In the third aspect of the instant claimed invention, it is necessary to extract the sample of water at a point before the water had been treated with scale inhibitor and in the fourth aspect it is necessary to add the Compound and use the fluorometer to measure the separate detectable fluorescent signal at a point before the water had been treated with scale inhibitor.

If the industrial water system is a boiler, then the analysis of possible locations to add the Compound is as follows.

The front end of the boiler system is referred to as the boiler make-up water treatment section of the boiler system. The types of equipment here include cold and hot lime softeners, sand and anthracite filters, possibly activated carbon filters, sodium zeolite ion exchange units, sometimes referred to as "cation exchange resin units in the sodium form", demineralizers (strong and/or weak cation exchangers in series with strong and/or weak anion exchangers, mix bed ion exchangers which are units that contain both cation and anion resins in the same vessel), reverse osmosis units, dealkalizers and electrodialysis units.

With the exception of hot lime softeners the operating temperature of the equipment in the boiler make-up water treatment section is ambient temperature. A hot lime softener operates at below 176.7° C. Therefore, no cooling of the water should be necessary before adding the Compound anywhere in the boiler make-up water treatment section.

The Compound could be injected/pumped into the effluent stream directly exiting these units to contact the entire water volume. The separate detectable fluorescent signal of the Compound can be detected, as long as the pH of the water is in the correct range such that the Compound develops a separate detectable fluorescent signal upon coming into contact with soluble hardness. In order to do this, a sample stream could be "run off" the main line into the fluorometer, as is described and claimed in the first, third and fifth aspects of the instant claimed invention.

If the pH of the water was below that required, then this side stream could be pH adjusted before the sample reaches the fluorometer Another way of conducting this method would be to inject the Compound into this sample stream ahead of the fluorometer and again pH adjust this stream if necessary. This means that all the water in the industrial water system would not be exposed to the Compound, only the sample of water that goes through the fluorometer would come into contact with the Compound.

Another factor is that the treated makeup water usually goes to a holding tank and the hardness of the water in that holding tank could be determined using the method of the instant claimed invention.

The next part of the boiler system is typically referred to as the boiler feedwater section. A known configuration of the boiler feedwater section is to have a deaerator, feedwater pumps, low and high temperature feedwater heaters and an economizer. A boiler system may have all of these or some of these. In some boiler systems there is no deaerator, only a hot water atmospheric heater and this water is pumped into the boiler that has no other feedwater heaters or economizer. As the boiler feedwater is pumped through the systems which have either low and high temperature feedwater heaters and/or an economizer, the temperature of the water will increase and depending on the maximum temperature limit of the Compounds, the Compounds may or may not be injected directly into the feedwater without first cooling the sample as is described in the second, fourth and sixth aspects of the instant claimed invention.

The typical temperature of the water in an atmospheric feedwater heater is about 90° C. (194° F.) so Compounds with an operability maximum temperature at or above this temperature may be injected directly into the water here without cooling. Deaerators (hereinafter "DA") generally operate between 3 psig to 60 psig (105° C./221° F. to 153° C./307° F.). The preferred point of addition would be to inject an internal boiler treatment product that contains the Compound into the storage section of the deaerator or into the pipe (DA dropleg) exiting the storage section. Down stream of this point (a minimum distance equal to approximately 10 pipe diameters) and usually before the feedwater pump is the place for a sample point that would allow a small portion of the Compound containing boiler feedwater to continuously flowing through a cooler and the cooled boiler feedwater sample then would go through the fluorometer. Typical feedwater pH's are 9.0 or above and thus probably will not need pH adjustment to see the fluorescence. If the pH happened to be lower than desired, then base could be added to this cooled sample stream to raise the pH to desired range. Using the method of the instant claimed invention means that the operator of the boiler system would have the capability to automate the boiler chemical treatment feed pump based on whether the fluorometer detected the separate detectable fluorescent signal of the Compound indicating that free soluble hardness is present. Also an alarm could be set to sound when this upset condition occurred.

There is a chance that the temperature of some DA's will be above that of the stability of the Compounds and thus the Compound would have to be injected into the cooled boiler feedwater sample ahead of the fluorometer as opposed to having the Compound formulated into an internal Boiler treatment product which would be fed to the DA or DA dropleg.

Other places that it would be possible to monitor the hardness down stream of the DA would be on the pressure side of the feedwater pump at the inlet of the economizer if the boiler had one. Again the temperature here might again require injecting the Compound into the cooled sample stream ahead of the fluorometer instead of having the Compound formulated into the internal treatment product.

The next part of the boiler system is the boiler itself. Most boilers have a continuous boiler water blowdown system and the plants have a cooled boiler water flowing sample point. The pH of the boiler water would be high enough to not have to adjust the pH before the fluorometer. If the boiler pressure is low enough then it would not be necessary to use the approach of separately injecting the Compound in the cooled boiler water sample but just have the internal boiler treatment product have the Compound in it. If the boiler temperature is above the maximum limit of operability of the Compound then the injection of the Compound into the cooled sample would be the method of adding the Compound.

The final section is the steam condensate system. Steam is used to generate electricity in certain cases. The steam will pass through a turbine and in some cases the steam exits the turbine and is fully condensed into liquid water. This type of turbine is known as a condensing turbine. In the condenser section there is cooling water either on the tube side or shell side, indirectly contacting the steam and cooling the steam to room temperature or lower in certain systems. In utilities, operators are extremely worried about condenser cooling water leaks developing and contaminating the steam condensate. The method of the instant claimed invention would work effectively here. The Compound could be fed directly into the condensate sample stream ahead of the fluorometer and if soluble hardness was present the fluorescent signal of the Compound would change and the fluorometer would detect the changed fluorescent signal.

Most steam condensate systems are complex and they contain many miles of piping and many local condensate receivers which collect condensate that is pumped back to a final (main) condensate receiver. The method of the instant claimed invention could be used in several different ways. First a Compound could be put into an injection/fluorometer monitoring system on a cooled flowing sample taken from the final condensate pipeline entering the main condensate receiver. If a cooling water leak developed in a remote area within the steam condensate system and this contamination reached the point where monitoring final condensate hardness quality was being monitored, the method of the instant claimed invention would detect it. An alarm could be set to activate to tell the operators that a hardness leak occurred. Potentially, this alarm could be linked to an automatic dump control system which would direct this contaminated condensate to the sewer instead of the receiver. This same scenario could be set up at different sections of the condensate system not only at the final receiver. This approach could be used on any known problematic area such as the condensate being returned from a paper machine or process unit or buildings etc.

The method of addition of the Compound to the water of the industrial water system depends upon what industrial water system is being treated and the Compound selected. The preferred industrial water system is a boiler.

The fluorometer used to detect the fluorescent signal of the Compound can be any commercially available fluorometer capable of detecting the separate detectable fluorescent signal of the Compound. Preferred fluorometers include the Trasar® 3000 fluorometer, the Trasar® 8000 fluorometer and the modular fluorometer available from NALCO as well as the Hitachi F-4500 fluorometer. It is to be understood that it may be necessary to reconfigure the fluorometer to optimize the set-up of the fluorometer so that it is possible to detect the separately detectable fluorescent signal of the Compound that only appears in the presence of soluble hardness. It is known to people of ordinary skill in the art of fluorometers how to set up a fluorometer to detect the separate detectable fluorescent signal. After the separate detectable fluorescent signal has been detected it is known how to convert the amount of fluorescent signal detected into the amount of soluble hardness present in the water.

If the separate detectable fluorescent signal is detected then there is sufficient soluble hardness present in the water to interact with the Compound. If no separate detectable fluorescent signal is detected, then there is not sufficient soluble hardness present in the water to interact with the Compound. This is the basis for the utility of the method of the instant claimed invention.

Because the method of the instant claimed invention can be used to determine the amount of soluble hardness present in the water of an industrial water system, the method can be used in conjunction with the feeding of a treatment product such that the desired amount of treatment product is fed. The treatment product typically contains a scale inhibitor, or a dispersant or both a scale inhibitor and a dispersant. The treatment product also is formulated to contain an inert tracer which is present in a known proportion to the other ingredients of the treatment product. By detecting and measuring the fluorescent signal of the inert tracer it is possible to verify the amount of treatment product that is being fed into the water of the industrial water system using fluorometric techniques known to people of ordinary skill in the art of tracers. This is the method of the third, fourth, fifth and sixth aspects of the instant claimed invention.

It has been found that only Selected Treatment Products interact with soluble hardness such that the soluble hardness is not available to interact with the Compound to form a moiety that has a separate detectable fluorescent signal. These Selected Treatment Products include the following: polyacrylates, polymethacrylates, acrylate styrene sulfonate copolymers, ethylenediaminetetraacetic acid, nitrilotriacetic acid, 1-hydroxyethylidene-1,1-diphosphonic acid, hexamethylenediamine hexametaphosphate, tripolyphosphate; polyphosphonates and known salts thereof.

These Selected Treatment Products are the ones that will work in the fifth and sixth aspect of the instant claimed invention. Preferred Selected Treatment Products for the fifth and sixth aspects of the instant claimed invention are polyacrylates, polymethacrylates, acrylate styrene sulfonate copolymers, ethylenediaminetetraacetic acid, nitrilotriacetic acid, 1-hydroxyethylidene-1,1-diphosphonic acid, hexamethylenediaminetetra methylene phosphonic acid and polyphosphonates.

If the water sample is extracted before the water is treated with treatment product or if the fluorometer is used on the water of the industrial water system at a point prior to the water being treated with treatment product then it is possible to use many more different types of treatment products. This is the method of the third and fourth aspects of the instant claimed invention.

The treatment products that can be used in the method of the third and fourth aspects of the instant claimed invention include the following: any anionic polymer that can effectively complex with magnesium; these anionic polymers include polyacrylates, polymethacrylates, and acrylate styrene sulfonate copolymers; chelants such as ethylenediaminetetraacetic acid, nitrilotriacetic acid, 1-hydroxyethylidene-1,1-diphosphonic acid, hexamethylenediaminetetra methylene phosphonic acid; phosphates such as hexametaphosphate, tripolyphosphate and ortho phosphate; polyphosphonates, natural and synthetic cationic polymers such as lignins, lignosulfonates, tannins, poly peptides, polyamines, quaternary amines, celluloses, starches, polymaleic anhydrides, polyvinyl sulfonates, inorganic phosphates, organic phosphates, inorganic carbonates, organic carbonates, various surfactants and known salts thereof.

Preferred treatment products for the third and fourth aspect of the instant claimed invention are polyacrylates, polymethacrylates, acrylate styrene sulfonate copolymers, ethylenediaminetetraacetic acid, nitrilotriacetic acid, 1-hydroxyethylidene-1,1-diphosphonic acid, hexamethylenediaminetetra methylene phosphonic acid, polyphosphonates, ortho phosphate, inorganic carbonates and known salts thereof.

It is possible when conducting any of the aspects of the instant claimed invention to formulate the Compound with a known amount of an inert fluorescent tracer. If this is done then the amount of Compound present in the water can be verified by using a fluorometer to detect the fluorescent signal of the inert tracer and converting the fluorescent signal to the amount of inert tracer present. If the amount of inert tracer present is known then the amount of Compound can be known as well because the inert tracer is present in a known proportion to the Compound. Inert tracers are known in the art of water treatment, see U.S. Pat. Nos. 4,783,314; 4,966,711; 4,992,380; 5,006,311; 5,043,406; 5,171,450; 5,278,074; 5,378,784; 5,389,548; 5,411,889; 5,413,719; 5,645,799; 5,658,798; 5,702,684; 5,714,387; 5,736,405; 5,919,707; 5,958,788; and 5,986,030, all of which are incorporated by reference. The preferred inert tracer for these Compounds is fluoroscein. Of course, if an inert tracer is used, then a fluorometer must be provided such that the fluorescent signal of the inert tracer can be measured. Any of the fluorometers previously described could be used for this purpose.

By practicing any of the aspects of the instant claimed invention it is possible to determine the level of soluble hardness present in the water of an industrial water system. By practicing the third, fourth, fifth and sixth aspects of the instant claimed invention it is possible to determine the level of soluble hardness present in the water of an industrial water system and use that information to control the feed rate of treatment product (third and fourth aspects) or Selected Treatment Product (fifth and sixth aspects) being added to the water.

The specific examples herein disclosed are to be considered as being primarily illustrative. Various changes beyond those described, will, no doubt, occur to those skilled in the art; and such changes are to be understood as forming a part of this invention insofar as they fall within the spirit and scope of the appended claims.

EXAMPLES

All initial fluorescence work on indicators for hardness monitoring was done on the Hitachi F-4500 fluorescence spectrophotometer, purchased from Hitachi.

Example I

Calmagite was examined as a potential Compound that could be used to fluorescently indicate the presence of soluble hardness. Calmagite was obtained from Aldrich. The Hitachi fluorometer was set at excitation (hereinafter "EX"), emission (hereinafter "EM") slits of 10.0 nm/10.0 nm and the photomultiplier tube (hereinafter "PMT") was set at 700 Volts (hereinafter "V"). Under basic conditions, pH of 11, a 10 ppm solution of Calmagite in deionized (hereinafter "DI") water with 5 ppm $Ca^{+2}$ as Ca and 5 ppm $Mg^{+2}$ as Mg (this simulates the level of soluble hardness found in some industrial water systems) exhibited a separate detectable fluorescence peak ("fluorescent signal") at 530 nm EX, 605 nm EM having fluorescence intensity of approximately 300 raw fluorescence units (hereinafter "RFU"). This peak was not evident in a pH adjusted 10 ppm solution of Calmagite with no hardness added.

A microspatula of EDTA crystals was then added to the solution with hardness. This caused the total loss of the separate detectable fluorescent signal at the 530 EX, 605 EM peak. Adding EDTA to the solution with hardness caused the fluorescent signal to disappear, indicating that the scale inhibitor ("EDTA") interacted with the soluble hardness present such that the soluble hardness was not available to interact with the Compound to form a moiety with a separate detectable fluorescent signal.

Example II

Plasmocorinth B was examined as a potential Compound that could be used to fluorescently indicate the presence of soluble hardness. Plasmocorinth B is available from Aldrich. The Hitachi fluorometer instrument parameters were set at EX, EM slits of 10.0 nm/10.0 nm and PMT was set at 700 V. Under basic conditions, pH of 11, a 10 ppm active dye solution with 10 ppm total hardness (5 ppm $Ca^{+2}$ as Ca and 5 ppm $Mg^{+2}$ as Mg) exhibited a separate detectable fluorescent peak ("fluorescent signal") at 550 nm EX, 595 nm EM with an intensity of 240 RFU. This separate detectable fluorescent peak was not evident in the solution without hardness.

Example III

Eriochrome® Blue Black B was examined as a potential Compound that could be used to fluorescently indicate the presence of soluble hardness. Eriochrome® Blue Black B is available from Aldrich. The Hitachi fluorometer instrument parameters were set at EX, EM slits of 10.0 nm/10.0 nm and PMT was set at 700 V. Under basic conditions, pH of 11.6, a 4 ppm active dye solution with the addition of 10 ppm Total Hardness exhibited a separate detectable fluorescence peak ("fluorescent signal") at 560 nm EX, 615 nm EM with an intensity of 1042 RFU. This peak was not evident in the solution without hardness. Adding EDTA to the solution with hardness caused the fluorescent signal to disappear, indicating that the scale inhibitor interacted with the soluble hardness present such that the soluble hardness was not available to interact with the Compound to form a moiety with a separate detectable fluorescent signal.

Example IV

Acid Alizarin Violet N was examined as a potential Compound that could be used to fluorescently indicate the presence of soluble hardness. Acid Alizarin Violet N is available from Aldrich. The Hitachi fluorometer instrument parameters were set at EX, EM slits of 10.0 nm/20.0 nm and PMT was set at 700 V. A 5 ppm active solution of Acid Alizarin Violet N with 10 ppm of Total Hardness that had been pH adjusted to approximately 12 exhibited a separate detectable fluorescence peak ("fluorescent signal") at 525 nm EX, 575 nm EM with an intensity of 372 RFU. This peak was not evident in the solution without hardness.

Although the invention has been described in detail for the purpose of illustration, it is to be understood that such detail is solely for that purpose and that numerous modifications, alterations and changes can be made therein by those skilled in the art without departing from the spirit and scope of the invention except as it may be limited by the claims. All changes which come within the meaning and range of equivalency of the claims are to be embraced within their scope.

What is claimed is:

1. A method of determining the amount of soluble hardness in the water of an industrial water system comprising the steps of:
   1) providing an industrial water system;
   2) providing a Compound, wherein said Compound is selected from the group of chemicals that develop a separate detectable fluorescent signal in the presence of soluble hardness;
   3) extracting a sample of water from the industrial water system and determining whether the sample of water is at or below the maximum temperature of operability of said Compound, and if the sample of water is above the maximum temperature of operability of said Compound, then cooling said sample of water until the temperature of the sample of water is at or below the maximum temperature of operability of said Compound;
   4) measuring the pH of the sample of water and determining whether the pH is between about 7.5 and about 13.5 and if the pH is not between about 7.5 and about 13.5, adjusting the pH of the sample of water such that the pH is between about 7.5 and about 13.5;
   5) adding to said sample of water from about 1 ppb to about 3,000 ppm of said Compound;
   6) providing a fluorometer;
   7) using said fluorometer to measure the separate detectable fluorescent signal of said Compound in said sample of water;
   8) using said separate detectable fluorescent signal to determine the amount of soluble hardness in said sample of water.

2. A method of determining the amount of soluble hardness in the water of an industrial water system comprising the steps of:
   1) providing an industrial water system wherein the pH of the water in said industrial water system is between about 7.5 and about 13.5;
   2) providing a Compound, wherein said Compound is selected from the group of chemicals that develops a separate detectable fluorescent signal in the presence of soluble hardness;
   3) adding to the water of the industrial water system from about 1 ppb to about 3,000 ppm of said Compound, wherein said Compound is added to the water of the industrial water system at a point where the water is at or below the maximum temperature of operability of said Compound;
   4) providing a fluorometer;
   5) using said fluorometer to measure the separate detectable fluorescent signal of said Compound in said water of said industrial water system;
   6) using said separate detectable fluorescent signal to determine the amount of soluble hardness in said water of said industrial water system.

3. A method of determining whether the appropriate level of treatment product, has been added to the water of an industrial water system comprising the steps of:

1) providing a treatment product, wherein said treatment product comprises scale inhibitor or dispersant or both, and an inert tracer in known proportions;
2) providing an industrial water system;
3) adding said treatment product to the water of said industrial water system;
4) providing a Compound, wherein said Compound is selected from the group of chemicals that develop a separate detectable fluorescent signal in the presence of soluble hardness;
5) extracting a sample of water from the industrial water system and determining whether the sample of water is at or below the maximum temperature of operability of said Compound, and if the sample of water is above the maximum temperature of operability of said Compound, then cooling said sample of water until the temperature of the sample of water is at or below the maximum temperature of operability of said Compound; wherein said sample of water is extracted from the industrial water system at a point where the water in the industrial water system has not had a treatment product added;
6) measuring the pH of the sample of water and determining whether the pH is between about 7.5 and about 13.5 and if the pH is not between about 7.5 and about 13.5, adjusting the pH of the sample of water such that the pH is between about 7.5 and about 13.5;
7) adding to said sample of water from about 1 ppb to about 3,000 ppm of said Compound;
8) providing at least one fluorometer;
9) using said fluorometer to measure the separate detectable fluorescent signal of said Compound in said sample of water;
10) using said separate detectable fluorescent signal to determine the amount of soluble hardness in said sample of water; and
11) increasing the feed rate of treatment product if step 10) shows there is an unacceptable level of soluble hardness present in the water and decreasing or maintaining the feed rate of treatment product if step 10) shows that an unacceptable level of soluble hardness is not present in the sample of water; wherein the amount of treatment product being fed into the water is verified by
 a) measuring the fluorescent signal of the inert tracer in said treatment product to determine how much inert tracer is present in the water; and
 b) using the amount of inert tracer present to determine the amount of treatment product that is being fed into the water.

4. A method of determining whether the appropriate level of treatment product has been added to the water of an industrial water system comprising the steps of:
1) providing a treatment product, wherein said treatment product comprises scale inhibitor or dispersant or both, and an inert tracer in known proportions;
2) providing an industrial water system wherein the pH of the water in said industrial water system is between about 7.5 and about 13.5;
3) adding said treatment product to the water of said industrial water system;
4) providing a Compound, wherein said Compound is selected from the group of chemicals that develops a separate detectable fluorescent signal in the presence of soluble hardness;
5) adding to the water of the industrial water system from about 1 ppb to about 3,000 ppm of said Compound, wherein said Compound is added to the water of the industrial water system at a point where the water is at or below the maximum temperature of operability of said Compound;
6) providing at least one fluorometer;
7) using said fluorometer to measure the separate detectable fluorescent signal of said Compound in said water of said industrial water system; wherein the measurement takes place at a point where the water in the industrial water system has not had a treatment product added;
8) using said separate detectable fluorescent signal of said Compound to determine the amount of soluble hardness in said water, increasing the feedrate of treatment product if step 7) shows there is an unacceptable level of soluble hardness present in the water and decreasing or maintaining the feed rate of treatment product if step 7) shows that an unacceptable level of soluble hardness is not present in the water; wherein the amount of treatment product being fed into the water is verified by:
 a) measuring the fluorescent signal of the inert tracer in said treatment product to determine how much inert tracer is present in the water; and
 b) using the amount of inert tracer present to determine the amount of treatment product that is present in the water.

5. A method of determining whether the appropriate level of Selected Treatment Product has been added to the water of an industrial water system comprising the steps of:
1) providing a Selected Treatment Product, wherein said Selected Treatment Product comprises Selected Scale Inhibitor or Selected Dispersant or both, and an inert tracer in known proportions;
2) providing an industrial water system;
3) adding said Selected Treatment Product to the water of said industrial water system;
4) providing a Compound, wherein said Compound is selected from the group of chemicals that develop a separate detectable fluorescent signal in the presence of soluble hardness;
5) extracting a sample of water from the industrial water system and determining whether the sample of water is at or below the maximum temperature of operability of said Compound, and if the sample of water is above the maximum temperature of operability of said Compound, then cooling said sample of water until the temperature of the sample of water is at or below the maximum temperature of operability of said Compound;
6) measuring the pH of the sample of water and determining whether the pH is between about 7.5 and about 13.5 and if the pH is not between about 7.5 and about 13.5, adjusting the pH of the sample of water such that the pH is between about 7.5 and about 13.5;
7) adding to said sample of water from about 1 ppb to about 3,000 ppm of said Compound;
8) providing at least one fluorometer;
9) using said fluorometer to measure the separate detectable fluorescent signal of said Compound in said sample of water;
10) using said separate detectable fluorescent signal to determine the amount of soluble hardness in said sample of water; and 11) increasing the feed rate of Selected Treatment Product if step 10) shows there is an unacceptable level of soluble hardness present in the water and decreasing or maintaining the feed rate of Selected Treatment Product if step 10) shows that an unacceptable level of soluble hardness is not present in the sample of water; wherein the amount of Selected Treatment Product being fed into the water is verified by
   a) measuring the fluorescent signal of the inert tracer in said Selected Treatment Product to determine how much inert tracer is present in the water; and
   b) using the amount of inert tracer present to determine the amount of Selected Treatment Product that is being fed into the water.

6. A method of determining whether the appropriate level of Selected Treatment Product has been added to the water of an industrial water system comprising the steps of:
   1) providing a Selected Treatment Product, wherein said Selected Treatment Product comprises Selected Scale Inhibitor or Selected Dispersant or both, and an inert tracer in known proportions;
   2) providing an industrial water system wherein the pH of the water in said industrial water system is between about 7.5 and about 13.5;
   3) adding said Selected Treatment Product to the water of said industrial water system;
   4) providing a Compound, wherein said Compound is selected from the group of chemicals that develops a separate detectable fluorescent signal in the presence of soluble hardness;
   5) adding to the water of the industrial water system from about 1 ppb to about 3,000 ppm of said Compound; wherein said Compound is added to the water of the industrial water system at a point where the water is at or below the maximum temperature of operability of said Compound;
   6) providing at least one fluorometer;
   7) using said fluorometer to measure the separate detectable fluorescent signal of said Compound in said water of said industrial water system;
   8) using said separate detectable fluorescent signal of said Compound to determine the amount of soluble hardness in said water, increasing the feedrate of Selected Treatment Product if step 7) shows there is an unacceptable level of soluble hardness present in the water and decreasing or maintaining the feed rate of Selected Treatment Product if step 7) shows that an unacceptable level of soluble hardness is not present in the water; wherein the amount of Selected Treatment Product being fed into the water is verified by:
      a) measuring the fluorescent signal of the inert tracer in said Selected Treatment Product to determine how much inert tracer is present in the water; and
      b) using the amount of inert tracer present to determine the amount of Selected Treatment Product that is present in the water.

7. The method of claim 1 in which said Compound is selected from the group consisting of
   benzenesulfonic acid, 4-hydroxy-3-{(2-hydroxy-1-naphthalenyl)azo}-, monosodium salt;
   1-Naphthalenesulfonic acid, 3-hydroxy-4-{(2-hydroxy-5-methylphenyl)azo}-;
   1-Naphthalenesulfonic acid, 3-hydroxy-4-{(1-hydroxy-2-naphthalenyl)azo}-, monosodium salt; and
   2,7-Naphthalenedisulfonic acid, 3-{(5-chloro-2-hydroxyphenyl)azo}-4,5-dihydroxy-, disodium salt.

8. The method of claim 2 in which said Compound is selected from the group consisting of
   benzenesulfonic acid, 4-hydroxy-3-{(2-hydroxy-1-naphthalenyl)azo}-, monosodium salt;
   1-Naphthalenesulfonic acid, 3-hydroxy-4-{(2-hydroxy-5-methylphenyl)azo}-;
   1-Naphthalenesulfonic acid, 3-hydroxy-4-{(1-hydroxy-2-naphthalenyl)azo}-, monosodium salt; and
   2,7-Naphthalenedisulfonic acid, 3-{(5-chloro-2-hydroxyphenyl)azo}-4,5-dihydroxy-, disodium salt.

9. The method of claim 3 in which said Compound is selected from the group consisting of
   benzenesulfonic acid, 4-hydroxy-3-{(2-hydroxy-1-naphthalenyl)azo}-, monosodium salt;
   1-Naphthalenesulfonic acid, 3-hydroxy-4-{(2-hydroxy-5-methylphenyl)azo}-;
   1-Naphthalenesulfonic acid, 3-hydroxy-4-{(1-hydroxy-2-naphthalenyl)azo}-, monosodium salt; and
   2,7-Naphthalenedisulfonic acid, 3-{(5-chloro-2-hydroxyphenyl)azo}-4,5-dihydroxy-, disodium salt.

10. The method of claim 4 in which said Compound is selected from the group consisting of
    benzenesulfonic acid, 4-hydroxy-3-{(2-hydroxy-1-naphthalenyl)azo}-, monosodium salt;
    1-Naphthalenesulfonic acid, 3-hydroxy-4-{(2-hydroxy-5-methylphenyl)azo}-;
    1-Naphthalenesulfonic acid, 3-hydroxy-4-{(1-hydroxy-2-naphthalenyl)azo}-, monosodium salt; and
    2,7-Naphthalenedisulfonic acid, 3-{(5-chloro-2-hydroxyphenyl)azo}-4,5-dihydroxy-, disodium salt.

11. The method of claim 5 in which said Compound is selected from the group consisting of
    benzenesulfonic acid, 4-hydroxy-3-{(2-hydroxy-1-naphthalenyl)azo}-, monosodium salt;
    1-Naphthalenesulfonic acid, 3-hydroxy-4-{(2-hydroxy-5-methylphenyl)azo}-;
    1-Naphthalenesulfonic acid, 3-hydroxy-4-{(1-hydroxy-2-naphthalenyl)azo}-, monosodium salt; and
    2,7-Naphthalenedisulfonic acid, 3-{(5-chloro-2-hydroxyphenyl)azo}-4,5-dihydroxy-, disodium salt.

12. The method of claim 6 in which said Compound is selected from the group consisting of
    benzenesulfonic acid, 4-hydroxy-3-{(2-hydroxy-1-naphthalenyl)azo}-, monosodium salt;
    1-Naphthalenesulfonic acid, 3-hydroxy-4-{(2-hydroxy-5-methylphenyl)azo}-;
    1-Naphthalenesulfonic acid, 3-hydroxy-4-{(1-hydroxy-2-naphthalenyl)azo}-, monosodium salt; and
    2,7-Naphthalenedisulfonic acid, 3-{(5-chloro-2-hydroxyphenyl)azo}-4,5-dihydroxy-, disodium salt.

13. The method of claim 3 in which said treatment product is selected from the group consisting of polyacrylates, polymethacrylates, acrylate styrene sulfonate copolymers, ethylenediaminetetraacetic acid, nitrilotriacetic acid, 1-hydroxyethylidene-1,1-diphosphonic acid, hexamethylenediaminetetra methylene phosphonic acid, hexametaphosphate, tripolyphosphate, ortho phosphate, polyphosphonates, lignins, lignosulfonates, tannins, poly peptides, polyamines, quaternary amines, celluloses, starches, polymaleic anhydrides, polyvinyl sulfonates, inorganic phosphates, organic phosphates, inorganic carbonates, organic carbonates, various surfactants and known salts thereof.

14. The method of claim 4 in which said treatment product is selected from the group consisting of polyacrylates, polymethacrylates, acrylate styrene sulfonate copolymers, ethylenediaminetetraacetic acid, nitrilotriacetic acid, 1-hydroxyethylidene-1,1-diphosphonic acid, hexamethylenediaminetetra methylene phosphonic acid, hexametaphosphate, tripolyphosphate, ortho phosphate, polyphosphonates, lignins, lignosulfonates, tannins, poly peptides, polyamines, quaternary amines, celluloses, starches, polymaleic anhydrides, polyvinyl sulfonates, inorganic phosphates, organic phosphates, inorganic carbonates, organic carbonates, various surfactants and known salts thereof.

15. The method of claim 5 in which said Selected Treatment Product is selected from the group consisting of polyacrylates, polymethacrylates, acrylate styrene sulfonate copolymers, ethylenediaminetetraacetic acid, nitrilotriacetic acid, 1-hydroxyethylidene-1,1-diphosphonic acid, hexamethylenediaminetetra methylene phosphonic acid, hexametaphosphate, tripolyphosphate, polyphosphonates and known salts thereof.

16. The method of claim 6 in which said Selected Treatment Product is selected from the group consisting of polyacrylates, polymethacrylates, acrylate styrene sulfonate copolymers, ethylenediaminetetraacetic acid, nitrilotriacetic acid, 1-hydroxyethylidene-1,1-diphosphonic acid, hexamethylenediaminetetra methylene phosphonic acid, hexametaphosphate, tripolyphosphate, polyphosphonates and known salts thereof.

17. The method of claim 1 in which the Compound is formulated with an inert tracer in known proportion and a fluorometer is used to detect the fluorescent signal of said inert tracer and the fluorescent signal of the inert tracer is used to determine how much inert tracer is present and by knowing how much inert tracer is present it is determined how much Compound is present in the sample of water.

18. The method of claim 2 in which the Compound is formulated with an inert tracer in known proportion and a fluorometer is used to detect the fluorescent signal of said inert tracer and the fluorescent signal of the inert tracer is used to determine how much inert tracer is present and by knowing how much inert tracer is present it is determined how much Compound is present in the water of the industrial water system.

19. The method of claim 3 in which the Compound is formulated with an inert tracer in known proportion and a fluorometer is used to detect the fluorescent signal of said inert tracer and the fluorescent signal of the inert tracer is used to determine how much inert tracer is present and by knowing how much inert tracer is present it is determined how much Compound is present in the sample of water.

20. The method of claim 4 in which the Compound is formulated with an inert tracer in known proportion and a fluorometer is used to detect the fluorescent signal of said inert tracer and the fluorescent signal of the inert tracer is used to determine how much inert tracer is present and by knowing how much inert tracer is present it is determined how much Compound is present in the water of the industrial water system.

21. The method of claim 5 in which the Compound is formulated with an inert tracer in known proportion and a fluorometer is used to detect the fluorescent signal of said inert tracer and the fluorescent signal of the inert tracer is used to determine how much inert tracer is present and by knowing how much inert tracer is present it is determined how much Compound is present in the sample of water.

22. The method of claim 6 in which the Compound is formulated with an inert tracer in known proportion and a fluorometer is used to detect the fluorescent signal of said inert tracer and the fluorescent signal of the inert tracer is used to determine how much inert tracer is present and by knowing how much inert tracer is present it is determined how much Compound is present in the water of the industrial water system.

23. The method of claim 1 in which said industrial water system is a boiler.

24. The method of claim 2 in which said industrial water system is a boiler.

25. The method of claim 3 in which said industrial water system is a boiler.

26. The method of claim 4 in which said industrial water system is a boiler.

27. The method of claim 5 in which said industrial water system is a boiler.

28. The method of claim 6 in which said industrial water system is a boiler.

* * * * *